United States Patent
Coers

Patent Number: 4,883,871
Date of Patent: Nov. 28, 1989

[54] PROCESS FOR THE PREPARATION OF 6-ALKYLTHIO-2,4-DIAMINO-1,3,5-TRIAZINES

[75] Inventor: Klaus J. Coers, Reinach, Switzerland

[73] Assignee: Ciba-Geigy Corporation, Ardsley, N.Y.

[21] Appl. No.: 240,167

[22] Filed: Sep. 2, 1988

[51] Int. Cl.$^4$ .......................................... C07D 251/52
[52] U.S. Cl. .................................................. 544/210
[58] Field of Search ........................................ 544/210

[56] References Cited

U.S. PATENT DOCUMENTS 3,558,622  1/1971  Rufener et al. ............... 260/249.8

FOREIGN PATENT DOCUMENTS 954528  4/1964  United Kingdom .

*Primary Examiner*—John M. Ford
*Attorney, Agent, or Firm*—Kevin T. Mansfield; Edward McC. Roberts

[57] ABSTRACT

6-Alkylthio-2,4-diamino-1,3,5-triazines of formula I

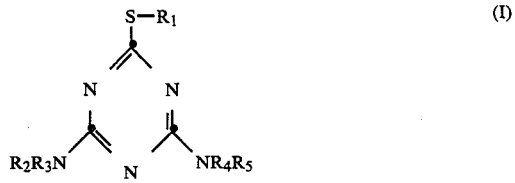

wherein
$R_1$ is $C_1$–$C_6$alkyl and
$R_2$, $R_3$, $R_4$ and $R_5$ are each independently hydrogen, $C_1$–$C_6$alkyl, allyl or $C_1$–$C_6$alkoxyalkyl,
are prepared by reacting 6-chloro-2,4-diamino-1,3,5-triazines of formula II

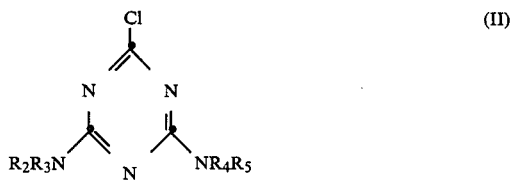

wherein $R_2$, $R_3$, $R_4$ and $R_5$ are as defined above, with a metal thioalkylate of formula III $M(SR_1)_n$ wherein
$R_1$ is as defined above,
n is 1 or 2, and
M is an alkali metal if n is 1 or an alkaline earth metal if n is 2, in the presence of a tertiary amine in a two-phase reaction medium consisting of water and an inert, organic, water-immiscible solvent.

20 Claims, No Drawings

PROCESS FOR THE PREPARATION OF 6-ALKYLTHIO-2,4-DIAMINO-1,3,5-TRIAZINES

The present invention relates to a process for the preparation of 6-alkylthio-2,4-diamino-1,3,5-triazines of the formula I

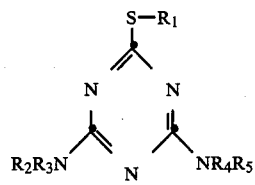

wherein
R$_1$ is C$_1$–C$_6$alkyl, and
R$_2$, R$_3$, R$_4$ and R$_5$ are each independently hydrogen, C$_1$–C$_6$alkyl, allyl or C$_1$–C$_6$alkoxyalkyl,
by reacting 6-chloro-2,4-diamino-1,3,5-triazines of formula II

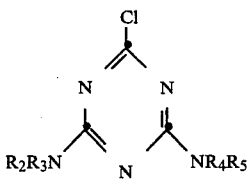

wherein R$_2$, R$_3$, R$_4$ and R$_5$ are as defined above, with a metal thioalkylate of formula III

     M(SR$_1$)$_n$     (III)

wherein
R$_1$ is as defined above,
n is 1 or 2, and
M is an alkali metal if n is 1 or an alkaline earth metal if n is 2.

Alkyl will be understood as meaning straight chain or branched alkyl. Suitable C$_1$–C$_6$alkyl radicals are for example: methyl, ethyl, n-propyl, isopropyl, n-butyl, isobutyl, sec-butyl, tert-butyl, n-pentyl or the isomers thereof, hexyl or the isomers thereof.

Alkoxyalkyl may be: methoxymethyl, methoxyethyl, methoxypropyl, ethoxyethyl, ethoxymethyl or propoxymethyl.

On account of their growth-inhibiting action on plants, 6-alkylthio-2,4-diamino-1,3,5-triazines of formula I can be used as herbicides. Examples of particularly useful herbicides are 2,4-diisopropylamino-6-methylthio-1,3,5-triazine (prometryn), 2-ethylamino-4-isopropylamino-6-methylthio-1,3,5-triazine (ametryn), 2-isopropylamino-4-methylamino-6-methylthio-1,3,5-triazine(desmetryn) and 2,4-diethylamino-6-methylthio-1,3,5-triazine (simetryn).

It is already known to prepare ametryn by reacting 6-chloro-2-ethylamino-4-isopropylamino-1,3,5-triazine (atrazine) with sodium thiomethylate in aqueous medium and in the temperature range from 120°–220° C. under a pressure commensurate with the reaction temperature (U.S. Pat. No. 3,558,622).

The drawback of this process is that the reaction mixture, even at elevated temperature (180° C.), becomes highly viscous and barely stirrable. In addition, pronounced hydrolysis occurs in the temperature range of 180° C. and the reaction no longer proceeds selectively. Furthermore, the high pressure of 10–15 bar is disadvantageous. Synthesis on an industrial scale therefore entails the use of complicated apparatus.

It is also known to prepare ametryn from atrazine by adding sodium thiomethylate to a mixture of atrazine, 84% aqueous isopropanol and 50% aqueous sodium hydroxide solution, then heating the reaction mixture for 3 hours under pressure to 80°–85° C., removing the isopropanol by distillation and isolating ametryn by filtration (q.v. Swiss Pat. No. 396 021).

In these processes, the excess of metal thioalkylate necessary for achieving an appropriate reaction rate is usually 30 mol %, based on the starting triazine of formula I. Recovery and disposal of the excess metal thioalkylate entails additional steps. A further shortcoming of these known processes is that, on account of the greater sensitivity to oxidation of the metal thioalkylates, the thioalkylation must be carried out in organic solutions, with the exclusion of atmospheric oxygen, so making it difficult to perform the reaction and necessitating the use of complicated apparatus.

The use of isopropanol as solvent for the starting compound of formula II in this known process does not permit the preparation of 6-alkylthio-2,4-diamino-1,3,5-triazines of formula I starting from cyanuric chloride in a single reaction vessel, as the 6-chloro-2,6-diamino-1,3,5-triazine obtained as intermdediate for the thioalkylation must first be isolated from the reaction medium - usually toluene.

By means of the known processes it is only possible to prepare 6-alkylthio-2,4-diamino-1,3,5-triazines of formula I with complicated and expensive installations and in an economically unsatisfactory manner. It is therefore the object of the present invention to provide a generally applicable process for the preparation of 6-alkylthio-2,4-diamino-1,3,5-triazines of formula I which, from the technical and economic aspect, constitutes an improvement over the prior art.

It has now been found that this object can be achieved in advantageous manner by carrying out the reaction of 6-chloro-2,4-diamino-1,3,5-triazines of formula II with metal thioalkylates of formula III to give a 6-alkylthio-2,4-diamino-1,3,5-triazine of formula I in the presence of a tertiary amine. Contrary to expectations, it has been found that the presence of the tertiary amine enables the reaction to proceed under atmospheric pressure and at low temperature, with almost quantitative conversion of the metal thioalkylate.

Accordingly, the present invention postulates preparing 6-alkylthio-2,4-diamino-1,3,5-triazines of formula I

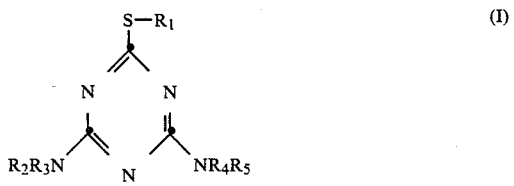

wherein R$_1$, R$_2$, R$_3$, R$_4$ and R$_5$ have the given meanings, by reacting 6-chloro-2,4-diamino-1,3,5-triazines of formula II

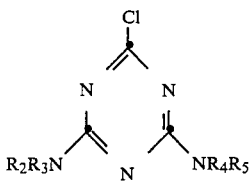

wherein $R_2$, $R_3$, $R_4$ and $R_5$ have the given meanings, with a metal thioalkylate of formula III

  M(SR$_1$)$_n$  (III)

wherein
$R_1$ is as defined above,
n is 1 or 2 and
M is an alkali metal if n is 1 or an alkaline earth metal if n is 2, in the presence of a tertiary amine, in a two-phase reaction medium consisting of water and an inert, organic, water-immiscible solvent.

Examples of tertiary amines are: quinuclidine, 1,4-diazabicyclo[2.2.2]-octane, 1,5-diazabicyclo[4.3.0]non-5-ene (DBN), 1,8-diazabicyclo[5.4.0]-undec-5-ene (DBU), N-methylpyrrolidine or N,N,N',N'-tetramethylethylenediamine. 1,4-Diazabicyclo[2.2.2]-octane, N-methylpyrrolidine and N,N,N',N'-tetramethylethylenediamine are preferred and 1,4-diazabicyclo[2.2.2]-octane is especially preferred.

The starting compounds of formula II are prepared in conventional manner by stepwise reaction of cyanuric chloride with the corresponding amines in a water-immiscible solvent, preferably toluene, in the presence of an aqueous solution of a base. In this reaction, after separation of the aqueous phase a suspension of a 6-chloro-2,4-diamino-1,3,5-triazine of formula II in a water-immiscible solvent is obtained, which solution is suitable for the carrying out the process of the invention direct. It is therefore advantageous to use the solution obtained in the preparation of the 6-chloro-2,4-diamino-1,3,5-triazine of formala II direct for carrying out the process of the invention.

For conveniently carrying out the process of this invention, an amount of 0.1 to 10% by weight of tertiary amine, based on the starting compound of formula II, has proved suitable. An amount of 0.25 to 0.35% by weight of tertiary amine, based on the starting compound of formula II, is especially preferred.

The process of the invention is conveniently carried out under atmospheric pressure in the temperature range from 50° to 120° C., preferably from 75° to 90° C.

Suitable inert, organic, water-immiscible solvents are open-chain or cyclic hydrocarbons, preferably n-hexane, toluene, xylene or cyclohexane. Also suitable are aliphatic ketones, preferably methyl ethyl kektone or methyl isopropyl ketone. Toluene is especially preferred.

A small excess of metal thioalkylate is used. An amount of 1.02 to 1.04 mol pe mol of compound of formula II is preferred.

A preferred embodiment of the process of this invention comprises carrying out the reaction of the 6-chloro-2,4-diamino-1,3,5-triazine of formula II with the metal thioalkylate of formula III in the presence of 1,4-diazabicyclo[2,2,2]-octane in the temperature range from 75° to 90° C. in a reaction medium consisting of water and toluene.

A further preferred embodiment of the process of the invention comprises carrying out the thioalkylation of a compound of formula II with an amount of 1.02 to 1.04 mol of sodium thioalkylate per mol of compound of formula II in the presence of 0.25 to 0.35% by weight of 1,4-diazabicyclo[2.2.2]-octane, based on the amount of compound of formula II.

In the above embodiment, compounds of formula I will preferably be prepared, wherein $R_1$ is methyl, $R_2$ and $R_4$ are hydrogen, and $R_3$ and $R_5$ are each independently of the other methyl, ehtyl, isopropyl or methoxypropyl, or $R_3$ is ethyl and $R_5$ is 1,2-dimethyl-n-propyl.

The process of this invention makes it possible to prepare 6-alkylthio-2,4-diamino-1,3,5-triazines of formula I in particularly simple manner and in good yield. For satisfactorily carrying out the process of the invention, an excess of only 2 to 4 mol % of metal thioalkylate, based on the triazine of formula II, will suffice. Other advantageous features of the process of this invention to be singled out are the low reaction temperatures and carrying out the reaction under atmospheric pressure.

A particular advantage of the process of this invention is that, starting from cyanuric chloride, compounds of formula I can be prepared on an industrial scale in a single reaction vessel.

PREPARATORY EXAMPLES

Example P1:

2-Ethylamino-4-isopropylamino-6-methylthio-1,3,5-triazine (ametryn) from atrazine With constant stirring, 147 g (1.04 mol) of a 50% solution of sodium thiomethylate are added dropwise over 1 hour at 80°–85° C. to a mixture of 217 g (1 mol) of 6-chloro-2-ethylamino-4-isopropylamino-1,3,5-triazine (atrazine), 217 g of toluene, 100 g of water and 0.6 g of 1,4-diazabicyclo-[2.2.2]-octane. After stirring for 2 hours at 80°–85° C., the organic phase is separated and the toluene removed by distillation, affording 223 g (98% of theory) of the title compound with a melting point of 85° C.

The title compound is also prepared in accordance with this Example using the following tertiary amines:
 (a) 4 g of N,N,N',N'-tetramethylethylenediamine
 (b) 1.5 g of N-methylpyrrolidine
 (c) 0.2 g of 1,4-diazabicyclo[2.2.2]octane (subsequent stirring time: 7 hours).

Example P2:

2-Ethylamino-4-isopropylamino-6-methylthio-1,3,5-triazine (ametryn) from cyanuric chloride (single vessel process) 184.5 g (1 mol) of 2,4,6-trichloro-1,3,5-triazine are added at 0°–5° C. to a mixture of 900 g of a 22% aqueous solution of sodium chloride and 200 g of toluene. Then 59.5 g (1 mol) of isopropylamine are added dropwise over 30 minutes to the above reaction mixture, whereupon the temperature rises to 20°–25° C. Then 80 g (1 mol) of a 50% aqueous solution of sodium hydroxide are added dropwise over 30 minutes. During the reaction the temperature is allowed to rise to 50° C.

After addition of 280 g of water, 45 g (1 mol) of ethylamine and 80 g of a 50% aqueous solution of sodium hydroxide are added dropwise to the reaction mixture, whereupon the temperature rises to 75° C.

After stirring for 30 minutes, the lower aqueous phase is separated. To the upper organic phase are added 100 g of water and 0.65 g of 1,4-diazabicylco[2.2.2]-octane.

Then 147 g (1.04 mol) of a 50% solution of sodium thiomethylate are added dropwise at 80°-85° C. over 1 hour to this reaction mixture. After stirring for 2 hours at 80°-85° C., the organic phase is separated and the toluene is removed by distillation, affording 223 g of the title compound which melts at 85° C.

What is claimed is:

1. A process for the preparation of a 6-alkylthio-2,4-diamino-1,3,5-triazine of formula I

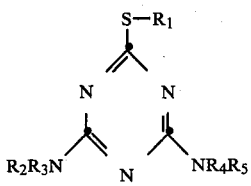

wherein
$R_1$ is $C_1$-$C_6$alkyl, and
$R_2$, $R_3$, $R_4$ and $R_5$ are each independently hydrogen, $C_1$-$C_6$alkyl, allyl or $C_1$-$C_6$alkoxyalkyl, by reacting a 6-chloro-2,4-diamino-1,3,5-triazine of formula II

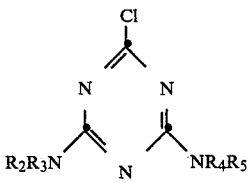

wherein $R_2$, $R_3$, $R_4$ and $R_5$ are as defined above, with a metal thioalkylate of formula III

$M(SR_1)_n$ wherein
$R_1$ is as defined above,
n is 1 or 2, and
M is an alkali metal if n is 1 or an alkaline earth metal if n is 2, which process comprises carrying out the reaction in the presence of a tertiary amine in a two-phase reaction medium consisting of water and an inert, organic, water-immiscible solvent.

2. A process according to claim 1, wherein the amount of tertiary amine is 0.1 to 10% by weight, based on the starting compound of formula II.

3. A process according to claim 1, wherein the metal thioalkylate of formula III is an alkali metal thioalkylate.

4. A process according to claim 1 which is carried out in the temperature range from 50° to 120° C.

5. A process according to claim 1, wherein the water-immiscible organic solvent is toluene, xylene, methyl ethyl ketone, methyl isobutyl ketone or cyclohexane.

6. A process according to claim 1, wherein the amount of tertiary amine is 0.25 to 0.35% by weight, based on the starting compound of formula II.

7. A process according to claim 1, wherein the tertiary amine is 1,4-diazabicyclo[2.2.2]-octane, N-methylpyrrolidine or N,N,N',N'-tetramethylethylenediamine.

8. A process according to claim 1 which is carried out in the temperature range from 75° to 90° C.

9. A process according to claim 1, wherein the metal thioalkylate is used in an amount of 1.02 to 1.04 mol per mol of starting compound of formula II.

10. A process according to claim 1, wherein the metal thioalkylate of formula II is a sodium thioalkylate.

11. A process according to claim 1, wherein $R_2$ and $R_4$ are hydrogen.

12. A process according to claim 1 which is carried out in the temperature range from 75° to 90° C. and wherein $R_1$ is methyl, M is sodium and $R_2$ and $R_4$ are hydrogen.

13. A process according to claim 12, wherein $R_3$ and $R_5$ are each independently of the other methyl, ethyl, isopropyl or methoxypropyl, or $R_3$ is ethyl and $R_5$ is 1,2-dimethyl-n-propyl, and $R_2$ and $R_4$ are hydrogen.

14. A process according to claim 1, wherein the tertiary amine is 1,4-diazabicyclo[2.2.2]-octane.

15. A process according to claim 14, wherein the metal thioalkylate is sodium thiomethylate.

16. A process according to claim 1 which is carried out in the presence of 0.25 to 0.35% by weight of 1,4-diazabicyclo[2.2.2]octane, based on the starting compound of formula II, and with 1.02 to 1.04 mol of metal thioalkylate of formula III per mol of starting compound of formula II, in the tempeature range from 75° to 90° C. in a medium consisting of water and toluene.

17. A prcess according to claim 16, wherein the metal thioalkylate is sodium thiomethylate.

18. A process according to claim 17, wherein $R_2$ and $R_4$ are hydrogen and $R_3$ and $R_5$ are each independently of the other methyl, ethyl, isopropyl or methoxypropyl, or $R_3$ is ethyl and $R_5$ is 1,2-dimethyl-n-propyl.

19. A process according to claim 1, wherein the solution of a 6-chloro-2,4-diamino-1,3,5-triazine of formula II in a water-immiscible solvent obtained in the synthesis of the compound of formula II from cyanuric chloride after separation of the aqueous phase is used direct for carrying out the process of the invention.

20. A process according to claim 19, wherein the water-immiscible solvent is toluene.

* * * * *